United States Patent [19]
Toth et al.

[11] Patent Number: 5,281,697
[45] Date of Patent: * Jan. 25, 1994

[54] CEA-BINDING PROTEIN AND USES THEREOF

[75] Inventors: Carol A. Toth, Sharon; Peter Thomas, Pembroke; Sibusisiwe M. Maswoswe, Ashland; Joseph V. Briggman, Westford, all of Mass.

[73] Assignees: Applied Biotechnology, Inc., Cambridge; New England Deacons Hospital Corp., Boston, both of Mass.

[*] Notice: The portion of the term of this patent subsequent to Sep. 14, 2010 has been disclaimed.

[21] Appl. No.: 708,888

[22] Filed: May 31, 1991

[51] Int. Cl.$^5$ .............. A61K 49/00; C07K 15/06; C07K 15/14; G01N 33/50
[52] U.S. Cl. .................. 530/350; 424/9; 436/64; 436/503; 436/543; 436/813; 530/387.7; 530/388.25; 530/389.3; 530/828
[58] Field of Search .............. 530/350, 395, 828, 412, 530/413, 415, 387.7, 387.9, 388.1, 388.25, 389.1, 389.3; 514/12, 13, 8, 21; 436/64, 503, 543, 544, 813; 424/9

[56] References Cited

U.S. PATENT DOCUMENTS

| | | | |
|---|---|---|---|
| 4,180,556 | 12/1979 | Kim et al. | 436/531 |
| 4,489,167 | 12/1984 | Ochi et al. | 436/518 |
| 4,579,827 | 4/1986 | Sakamoto et al. | 436/536 |
| 4,732,862 | 3/1988 | Bartorelli | 436/540 |
| 4,782,014 | 11/1988 | Serban et al. | 530/411 |
| 4,818,682 | 4/1989 | Linnane | 435/723 |
| 4,892,933 | 1/1990 | Salem et al. | 530/808 |
| 4,914,021 | 4/1990 | Toth et al. | 530/387 |

OTHER PUBLICATIONS

The Proteins, 3rd ed., published 1975, Neurath et al., vol. I, pp. 179, 180, 191.
Krupey et al. (1972) Immunochem. 9:617–622.
Rudman et al. (1972) Cancer Res. 32:1951–1959.
Pepys et al. (1978) Nature 273:168–170.
Thompson et al. (1978) Biochem. 17:4304–4311.
Pepys et al. (1979) Nature 278:259–261.
Beer et al. (1982) J. Immuno. Meth. 50:17–31.
Fink et al. (1982) Cancer Res. 42:1574–1578.
Kurzinger et al. (1982) J. Biolog. Chem. 257:12412–12418.
Ochi et al. (1982) Clin. Chem. Acta 122:145–160.
Ochi et al. (1982) J. Immunol. Meth. 52:213–221.
Pepys (1982) Eur. J. Rheumatol. Inflamm. 5:386–397.
Ziegler et al. (1982) Cancer Res. 42:1567–1573.
Kawasaki et al. (1983) J. Biochem. 94:937–947.
Wagener et al. (1983) J. Immunol. 130:230B–2315.
Blaszczyk et al. (1984) Cancer Res. 44:245–253.
Lei et al. (1985) J. Biolog. Chem. 260:13377–13383.
Mantzouranis et al. (1985) J. Biolog. Chem. 260:7752–7756.
Potempa et al. (1985) J. Biolog. Chem. 260:12142–12147.
Prelli et al. (1985) J. Biolog. Chem. 260:12895–12898.
Toth et al. (1985) Cancer Res. 45:392–397.

(List continued on next page.)

*Primary Examiner*—Jeffrey E. Russel
*Attorney, Agent, or Firm*—Lahive & Cockfield

[57] ABSTRACT

Disclosed is a protein that specifically binds carcinoembryonic actigen (CEA) in the presence of divalent cation in vitro. This protein has a molecular weight of about 20 kD as determined by SDS-polyacrylamide gel electrophoresis, is glycosylated, and includes the amino acid sequence set forth in the Sequence Listing as SEQ ID NO:4. Also disclosed are antibodies that recognize the CEA binding protein, methods of detecting carcinoma, methods of treating carcinoma, and a kit for screening a patient for carcinoma.

25 Claims, 8 Drawing Sheets

OTHER PUBLICATIONS

Ura et al. (1985) Cancer Letters 25:283–295.
Levo et al. (1986) Scan. J. Immunol. 24:147–151.
Ohnishi et al. (1985) J. Biochem. 100:849–858.
DeLellis et al. (1987) Seminars Oncol. 14:173–192.
Maudsley et al. (1987) J. Immunol. 62:17–22.
Niles et al. (1987) Cancer Investig. 5(6):545–552.
Salem et al. abstract, Proceedings of AACR (Mar., 1987) abstract No. 1571, 28:396.
Salem et al. (1987) Oncol. and Assoc. Immunol., pp. 408–410.
Toth et al. (1987) abstract, Am. Soc. Biol. Chemists, No. 110, p. 2116.
Toth et al. (1988) abstract FASEB.
Search Report (DIALOG).
Thomas et al. (1988) abstract FASEB abstract No. 1897, 2:A–623.
Prelli et al., "The Primary Structure of Human Tissue Amyloid P Component . . . ", *J. Biol. Chem.* 260(24) Oct. 25, 1985.
Toth et al. "A Carcinoembryonic Antigen (CEA) Binding Protein From Ascites . . . ", *Biochem. Biophys. Res. Comm.* 171(2) Sep. 14, 1990, ppp. 633–640.

COMPARISON OF CRP and the 20 kD and 21 kD CBP

```
Met Glu Lys Leu Leu Leu Cys Phe Leu Val Leu
 1           5                       10

21 kD CBP --> *   Thr Asp
Thr Ser Leu Ser His Ala Phe Gly Gln Thr Asp
            20 kD CBP --> Phe Gly Gln Thr Leu
            15                  20

Leu Ser Gly Lys Val Phe Val Phe Pro *   Glu
Met Ser Arg Lys Ala Phe Val Phe Pro Lys Glu
Met Gly Gly Lys Ala Phe Val Phe Pro Lys Ser
            25                  30

Ser Val Thr Asp *   Val Asn Leu Ile Thr Pro
Ser Asp Thr Ser Tyr Val Ser Leu Lys Ala Pro
        35                  40

Leu Glu Lys Pro Leu Gln *   Phe Thr *   Ser
Leu Thr Lys Pro Leu Lys Ala Phe Thr Val Cys
 45                  50                  55

*   *   Ala Tyr
Ley His Phe Tyr Thr Glu Leu Ser Ser Thr Arg
                    60                  65

Gly Tyr Ser Ile Phe Ser Tyr Ala Thr Lys Arg
                70                  75

Gln Asp Asn Glu Ile Leu Ile Phe Trp Ser Lys
            80                  85

Asp Ile Gly Tyr Ser Phe Thr Val Gly Gly Ser
        90                  95

Glu Ile Leu Phe Glu Val Pro Glu Val Thr Val
100                 105                 110
```

FIG. 5A

Ala Pro Val His Ile Cys Thr Ser Trp Glu Ser
            115               120

Ala Ser Gly Ile Val Glu Phe Trp Val Asp Gly
            125               130

Lys Pro Arg Val Arg Lys Ser Leu Lys Lys Gly
            135               140

Tyr Thr Val Gly Ala Glu Ala Ser Ile Ile Leu
145               150

Gly Gln Glu Gln Asp Ser Phe Gly Gly Asn Phe
155               160               165

Glu Gly Ser Gln Ser Leu Val Gly Asp Ile Asp
                170               175

Asn Val Asn Met Trp Asp Phe Val Leu Ser Pro
            180               185

Asp Glu Ile Asn Thr Ile Tyr Leu Gly Gly Pro
            190               195

Phe Ser Pro Asn Val Leu Asn Trp Arg Ala Leu
    200               205

Lys Tyr Glu Val Gln Gly Glu Val Phe Thr Lys
210               215               220

Pro Gln Leu Trp Pro
                225

NOTE: * indicates amino acids which the computer could not identify, most probably Cys, His, Arg, or Trp.

*FIG. 5B*

COMPARISON OF SAP and the 20 kD and 21 kD CBP

Met Asn Lys Pro Leu Leu Trp Ile Ser Val Leu
 1            5                   10

21 kD CBP --> *   Thr Asp
Thr Ser Leu Leu Glu Ala Phe Ala His Thr Asp
         20 kD CBP --> Phe Gly Gln Thr Leu
            15                   20

Leu Ser Gly Lys Val Phe Val Phe Pro *   Glu
Leu Ser Gly Lys Val Phe Val Phe Pro Arg Glu
Met Gly Gly Lys Ala Phe Val Phe Pro Lys Ser
            25                   30

Ser Val Thr Asp *   Val Asn Leu Ile Thr Pro
Ser Val Thr Asp His Val Asn Leu Ile Thr Pro
       35                   40

Leu Glu Lys Pro Leu Gln *   Phe Thr *   Ser
Leu Glu Lys Pro Leu Gln Asn Phe Thr Leu Cys
       45                   50                   55

*   *   Ala Tyr
Phe Arg Ala Tyr Ser Asp Ley Ser Arg Ala Tyr
                   60                   65

Ser Leu Phe Ser Tyr Asn Thr Gln Gly Arg Gly
            70                   75

Asn Glu Leu Leu Val Tyr Lys Glu Arg Val Gly
            80                   85

Glu Tyr Ser Leu Tyr Ile Gly Arg His Lys Val
       90                   95

Thr Ser Lys Val Ile Glu Lys Phe Pro Ala Pro
100                 105                 110

*FIG. 6A*

Val His Ile Cys Val Ser Trp Glu Ser Ser Ser
               115                    120

Gly Ile Ala Glu Phe Trp Ile Asn Gly Thr Pro
            125                 130

Leu Val Lys Lys Gly Leu Arg Gln Gly Tyr Phe
        135                 140

Val Gle Ala Gln Pro Lys Ile Val Leu Gln Gly
        145             150

Glu Gln Asp Ser Tyr Gly Gly Lys Phe Asp Arg
155                 160                 165

Ser Gln Ser Phe Val Gly Glu Ile Gly Asp Leu
            170                     175

Tyr Met Trp Asp Ser Val Leu Pro Pro Glu Asn
            180                 185

Ile Leu Ser Ala Tyr Gln Gly Thr Pro Leu Pro
            190             195

Ala Asn Ile Leu Asp Trp Gln Ala Leu Asn Tyr
        200             205

Glu Ile Arg Gly Tyr Val Ile Ile Lys Pro Leu
210                 215                 220

Val Trp Val

NOTE: * indicates amino acids which the computer could not identify, most probably Cys, His, Arg, or Trp.

*FIG. 6B*

CEA-BINDING PROTEIN AND USES THEREOF

REFERENCE TO RELATED APPLICATIONS

This application is related to applicants' copending U.S. patent applications Ser. No. 708,885, entitled "Method for Isolating CEA-Binding Protein" and U.S. Ser. No. 714,386, entitled "Binding Protein for CEA and Uses Thereof", both filed on even date herewith.

BACKGROUND OF THE INVENTION

The present invention relates to the field of cancer diagnosis and treatment, and more particularly to methods of detecting and treating carcinoma that elicit carcinoembryonic antigen (CEA). In particular, this invention relates to the identification of new cancer markers, CEA binding proteins, and methods of isolating such CEA-binding proteins, antibodies specific for these proteins, as well as methods useful in the diagnosis, detection, and monitoring of carcinoma.

Colorectal carcinoma is a cancer which affects approximately 600,000 additional people worldwide per year. The prognosis is poor in about 50% of the cases because the tumor is often not detected until the disease has spread and has reached a terminal stage. Early diagnosis is important to increase chances of arresting the carcinoma before it metastasizes, thereby leading to an improved prognosis.

A widely used method of the identification of cancerous tissue is to determine its structural resemblance to fetal or immature tissue. In this way, tumors can be classified depending on the degree of cellular differentiation; they can be undifferentiated, poorly differentiated, moderately differentiated or well differentiated. In addition, the behavior of a given tumor can often be related to its degree of differentiation. For example, poorly differentiated tumors tend to grow more rapidly and metastasize earlier than do differentiated tumors which more closely resemble the tissue of origin. Poorly differentiated tumors tend to have a poor prognosis and are difficult to detect.

One method of early tumor diagnosis is detection of the presence of a marker or antigen specific for a particular tumor. These normally proteinaceous markers are synthesized by the tumor, and may be found in the serum and/or on the surface of the tumor. Only a limited number of tumor markers for colorectal carcinoma have thus far been found to have clinical use. These include CEA and the sialyated Lewis a antigen (CA 19.9). Unfortunately, approximately 40% of patients whose condition has been accurately diagnosed as colorectal carcinoma do not have elevated plasma levels of either of these antigens when initially examined. In the case of CEA, this may be because this antigen is so rapidly cleared from the circulation. Recently, however, two new cancer markers, the carcinoma orosomucoid-related antigen (CORA) (U.S. Pat. No. 4,914,021) and the CC-glycoprotein (U.S. Pat. No. 4,921,789) have been discovered by applicants. However, there is no commercially available serodiagnostic marker which can be used to detect the tumor and to monitor therapy for this group.

Production of some tumor markers e.g., CEA and CA 19.9, by tumor cells in vitro correlates with a greater degree of cellular differentiation. For example, CEA and CA 19.9 are present to a far lesser degree on poorly differentiated or undifferentiated cancer cells than on those which are more differentiated. Accordingly, many patients with undifferentiated colorectal carcinomas never develop elevated serum levels of either of these markers, even in the terminal stages of the cancer. There is also considerable overlap between the presence of CA 19.9 and CEA, the patient with a normal CEA level and an elevated level of CA 19.9 being the exception rather than the rule. Therefore, new markers suitable for identifying and monitoring undifferentiated tumors would be of great value.

Accordingly, it is an object of this invention to provide new markers for the detection of carcinoma.

It is another object of the invention to provide new markers suitable for diagnosing and monitoring, and treatment of carcinoma.

Yet another object is to provide antibodies specific for these new markers.

Still another object is to provide a method of isolating CEA-binding proteins that eliminates contamination by CEA.

A further object of the present invention is to provide a method and kit for the detection and monitoring of carcinoma in patients using antibodies specific for markers on carcinoma cells.

Yet another object of the invention is to provide a hybridoma which produces a monoclonal antibody that recognizes both undifferentiated and poorly differentiated carcinoma cells.

A still further object is to provide screening procedures for detecting the presence of carcinoma cells at all stages of differentiation.

These and other objects of the invention will be apparent from the description, drawing and claims which follow.

SUMMARY OF THE INVENTION

New tumor markers for carcinoma have been discovered which have the ability to bind CEA. These markers include two CEA-binding proteins (CBPs) having molecular weights of about 20,000 daltons (20 kD) and about 21 kD as determined by sodium dodecyl sulfate-polyacrylamide electrophoresis (SDS-PAGE), and binding CEA in vitro in the presence of a divalent cation. The 20 kD protein includes the amino acid sequence set forth in the Sequence Listing as SEQ ID NO:4. The 21 kD protein is glycosylated and includes the amino acid sequence set forth in the Sequence Listing as SEQ ID NO:2.

This invention also encompasses CEA-binding fragments of these tumor markers. The term "CEA-binding protein" or "CBP" is used herein to describe both proteins and fragments thereof which bind CEA.

In one embodiment of the invention, the 20 kD or 21 kD CBP further includes a label, such as one selected from the group consisting of radioactive isotopes, enzymes, stable free radicals, coenzymes, fluorescent groups, chemiluminescent groups, toxins, and colorimetric groups. In another embodiment, the 20 kD or 21 kD CBP is bound to a support which forms a device useful, for example, in purifying CEA.

In yet another embodiment, antibodies and binding fragments thereof specific for a CBP are provided. Preferably, the antibody is a monoclonal antibody. The antibody can form part of a kit for screening a patient for carcinoma. This kit further includes an antibody specific for a carcinoma marker selected from the group consisting of carcinoma orosomucoid-related antigen (CORA), the CC glycoprotein, carcinoembryonic antigen (CEA), CA 19.9, non-specific cross-reacting antigen (NCA), and alpha 1-acid glycoprotein (AGP), serum amyloid P protein (SAP), and C-reactive protein (CRP).

The invention also provides methods of isolating and using CBPs. More specifically, a method of isolating a CBP, such as the 20 kD, the 21 kD, or any CBP that binds CEA in vitro in the presence of a divalent cation, is provided which includes the following steps. A biological sample containing CEA and a CBP is provided. The biological sample may be ascites fluid, whole blood, serum, bile, saliva, sputum, lymphoid tissue, or tumor tissue obtained from a subject afflicted with carcinoma. This sample is contacted with a divalent cation, such as $Ca^{+2}$, $Zn^{+2}$, or $Mg^{+2}$, at a concentration and for a time sufficient to enable the CBP to bind to CEA, thereby forming a CBP-CEA conjugate. The sample is contacted with an adsorbent that binds CEA, such as an immobilized immunoadsorbent including an antibody to CEA, for a time sufficient to allow the conjugate to adsorb to the adsorbent. Portions of the sample which have not adsorbed to the adsorbent are removed. The CBP is then dissociated from the adsorbent-bound conjugate. Dissociation can be accomplished with the use of an agent that chelates divalent cations such as ethylenediaminetetraacetic acid (EDTA) or ethylene glycol-bis[$\beta$-aminoethyl ether]-N,N,N',N'-tetraacetic acid (EGTA). The dissociated CBP is then collected, for example, by executing a purification method such as high pressure liquid chromatography (HPLC), SDS-PAGE, affinity chromatography, exclusion chromatography, ammonium sulfate precipitation, ultracentrifugation, and/or isoelectric focusing. For samples which do not contain CEA, CBP can be isolated by added CEA to the sample, or by reading the sample with CEA immobilized on a solid support in the presence of a divalent cation.

A method of detecting carcinoma is provided which includes the following steps. A pharmaceutical formulation including the 20 kD or 21 kD CBP, or CEA-binding fragments thereof, is administered in a physiologically acceptable carrier to the subject. A biological sample is taken and the concentration of CEA assayed for CEA. The concentration of CEA is then compared with a predetermined threshold level of CEA indicative of the presence of carcinoma.

Another aspect of the invention includes a method of screening for carcinoma including subjecting a biological sample from a subject to a test, such as an immunoassay, indicating the presence of a cancer marker, and screening the sample for the presence of a CBP, its presence being indicative of the presence of carcinoma.

Other embodiments of the invention include assay formats detecting CEA in a body fluid by adsorbing CBP to a support (such as a microtiter plate, for example) treating the body fluid to be screen with divalent cation, adding the treated body fluid to the CBP-bound plate, and then quantitating the bound CEA with labelled anti-CEA antibody. Alternatively, anti-CEA antibody can be adsorbed to the support which is then treated with the body sample in the presence of divalent cation. The presence of complexed CEA (or CBP to which the CEA in the body sample is complexed in the presence of divalent cation) can then be detected by treatment with labelled anti-CBP antibody. CBPs free in body samples can be detected by adsorbing CEA to a support, and then treating the support with the body sample in the presence of divalent cation.

Also provided is a method of treating carcinoma. This method includes providing a CBP and administering it in a pharmaceutically acceptable carrier to a subject afflicted with carcinoma. The CBP binds CEA present in the subject, thereby inhibiting the metastatic proliferation of carcinoma cells which occurs as a result of CEA binding to CEA receptors on various organs. The provision of the CBP can be accomplished by recombinant DNA technology, automated or manual biochemical peptide synthesis, or by purification from a subject inflicted with carcinoma.

BRIEF DESCRIPTION OF THE DRAWING

The foregoing and other objects of this invention, the various features thereof, as well as the invention itself may be more fully understood from the following description when read together with the accompanying drawings in which:

FIG. 5 is a comparison of the amino acid sequences of C-reactive protein and the 20 kD and 21 kD CBPs; and FIG. 6 is a comparison of the amino acid sequences of serum amyloid P protein and the 20 kD and 21 kD CBPs.

DESCRIPTION OF THE INVENTION

Proteins that influence the concentration of CEA in the blood have been isolated from patients afflicted with carcinoma. These CEA-binding proteins are also markers for carcinoma, and as such are useful in the detection and treatment of carcinoma.

Figure 1:
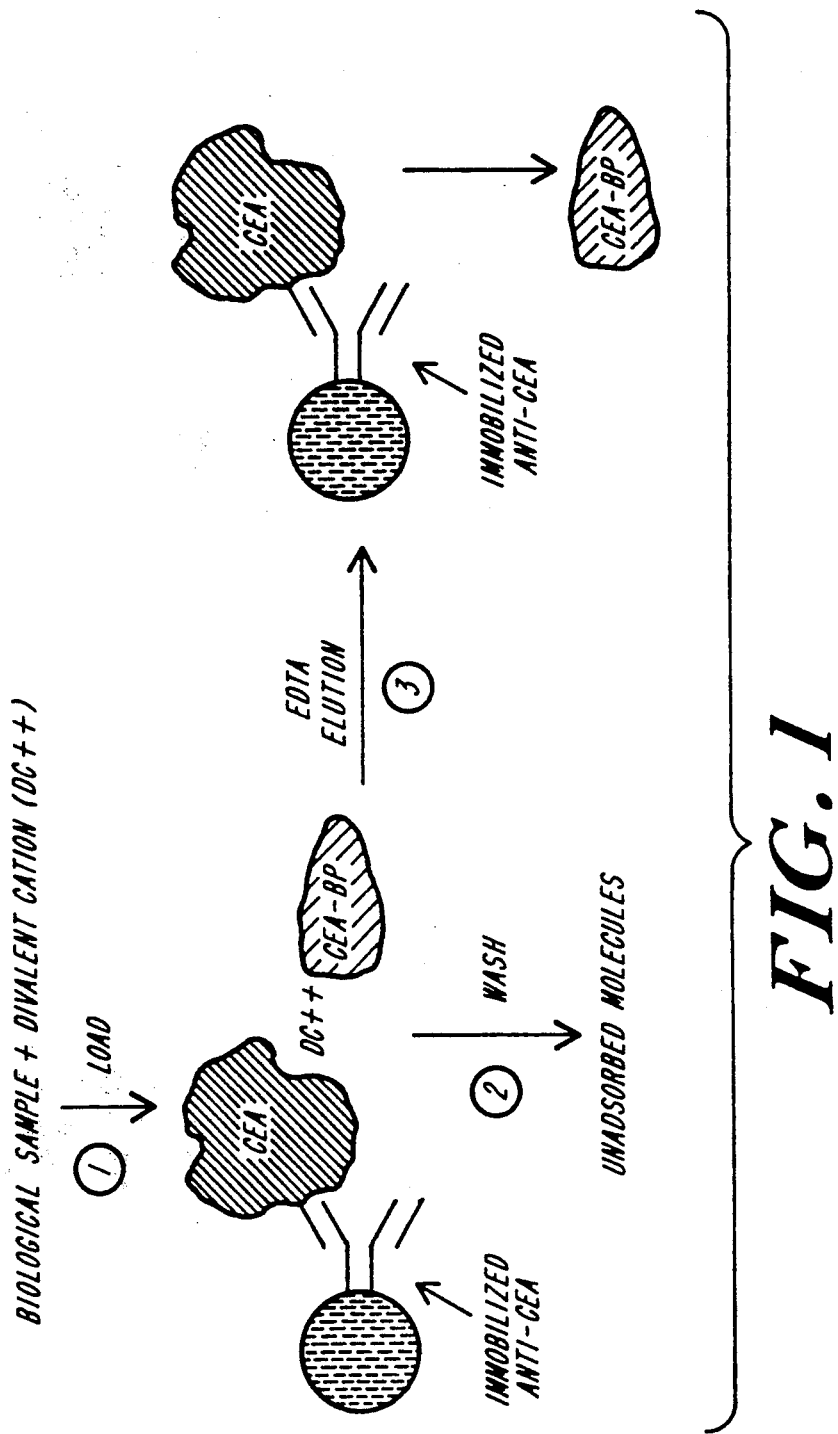
FIG. 1 is a diagrammatic representation of the CBP purification scheme of the invention.

The CBPs have been isolated using a purification method which virtually eliminates contamination by CEA. This procedure is schematically represented in FIG. 1. A biological sample containing CEA and CBP is provided. The biological sample may be ascites fluid, whole blood, serum, bile, saliva, sputum, lymphoid tissue, or tumor tissue obtained from a subject afflicted with carcinoma. This sample is contacted with a divalent cation, such as $Ca^{+2}$, $Zn^{+2}$, or $Mg^{+2}$, at a concentration and for a time sufficient to enable the CBP to bind to CEA, thereby forming a CBP-CEA conjugate. The sample is contacted with an adsorbent that binds CEA, such as an immobilized immunoadsorbent including an antibody to CEA, for a time sufficient to allow the conjugate to adsorb to the adsorbent. Portions of the sample which have not adsorbed to the adsorbent are removed. The CBP is then dissociated from the adsorbent-bound conjugate. Dissociation can be accomplished with the use of an agent that chelates divalent cations such as ethylenediaminetetraacetic acid (EDTA) or ethylene glycol-bis[$\beta$-aminoethyl ether]-N,N,N',N'-tetraacetic acid (EGTA). The dissociated CBP is then collected, for example, by executing a purification method such as high performance liquid chromatography (HPLC), SDS-PAGE, affinity chromatography, exclusion chromatography, ammonium sulfate precipitation, ultracentrifugation, and/or isoelectric focusing.

The instant purification procedure does not depend on the size of the binding protein, a particularly important point since CBPs isolated by this method have a molecular weight (by HPLC) similar to that of alpha-1 acid gylcoprotein (AGP). The procedure is ligand-specific, and thus any proteins that may bind to CEA nonspecifically or which require some other binding factors will not contaminate the product. Any contaminates are removed during the washing or will remain bound to CEA after the EDTA elution. This method also provides an effective way to isolate CBPs from CEA to which they have bound. Because CEA is a large molecule and very immunogenic, it is important to remove it from the CBP isolate if antibodies to these CBPs are to be prepared from the isolate.

Figure 2:
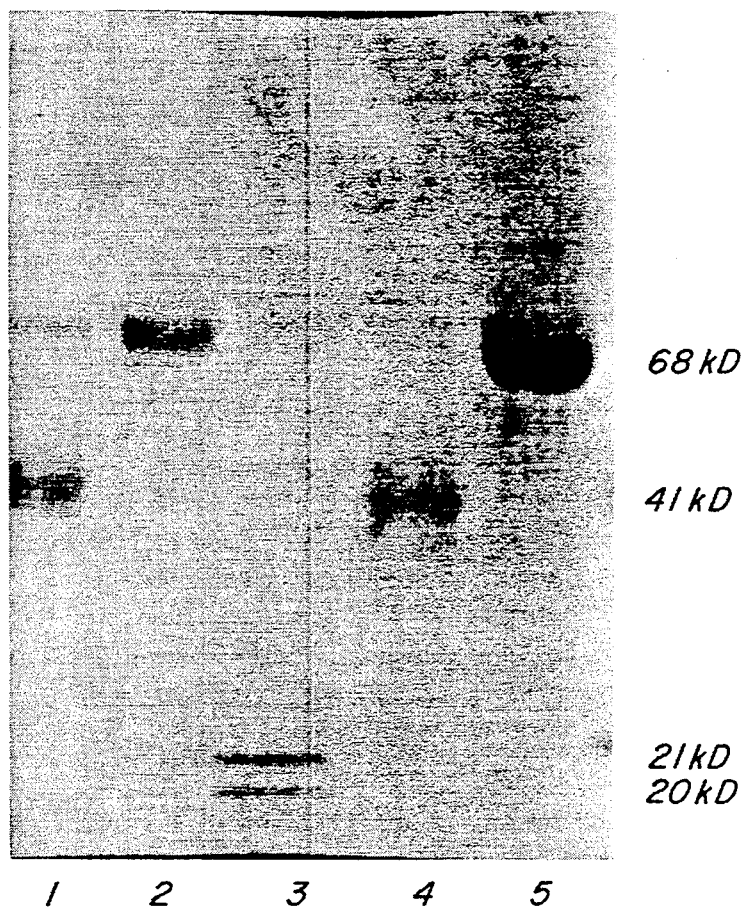
FIG. 2 is a photographic representation of a stained transfer blot of an SDS gel showing the 20 kD and 21 kD CBPs (lane 3), alpha 1-acid glycoprotein (lanes 1 and 4), column wash (lane 2), and human serum albumin (lane 5)

Using this method, two CBPs were isolated, one having a molecular weight of 20 kD and one glycoprotein having a molecular weight of 21 kD, as shown in FIG. 2, lane 3, of a stained transfer blot of an SDS-PA gel. These molecular weights differ from those of other known CEA binding proteins such as the 46-50 kD carcinoma orosomucoid-related antigen (CORA) (described in U.S. Pat. No. 4,914,021), and also differ from the 41 kD alpha 1-acid glycoprotein (AGP) which does not bind CEA.

Figure 3A:
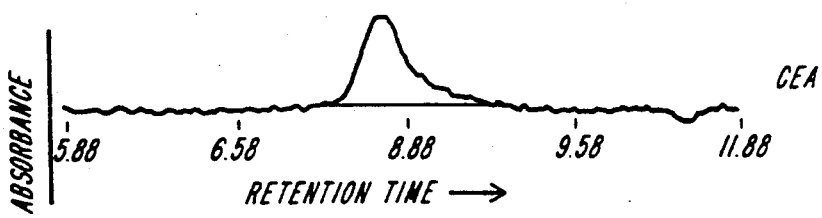
FIG. 3A–D is an optical scan of an HPLC of (A) CEA, (B) CBP 41 kD complex, (C) CEA+CBP in the presence of $CaCl_2$, and (D) CEA+CBP in the presence of EDTA.
Figure 3B:
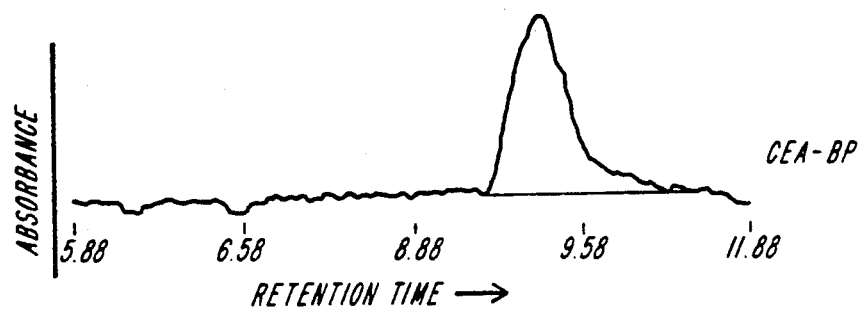
Figure 3C:
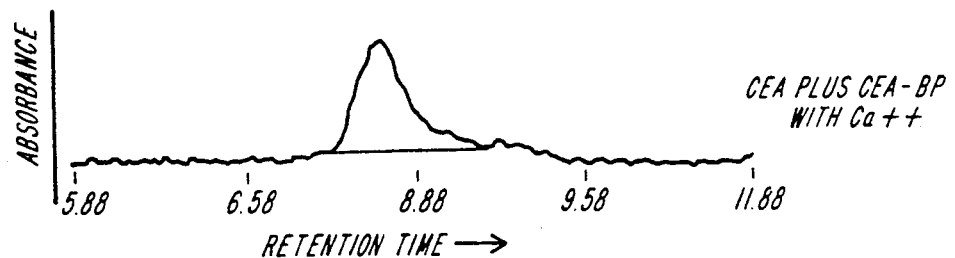

The physical properties of the 20 kD and 21 kD CBPs, as well as the degree of purity after isolation, were determined by high pressure liquid chromatography (HPLC). FIGS. 3A-3D show that the proteins isolated have a collective molecular weight of 41 kD (FIG. 3B). The appearance of a single peak with a retention time of about 8.5 min and the absence of a peak at about 9.4 min suggests the formation of a complex between CEA and CBP in the presence of calcium ions (FIG. 3C). However, in the presence of a calcium chelator like EDTA for example, two peaks with retention times similar to that of CEA (FIG. 3A) and that of the uncomplexed CBPs (FIG. 3B) were observed (FIG. 3D), indicating that these CBPs do not bind CEA in the absence of calcium.

Figure 4A:
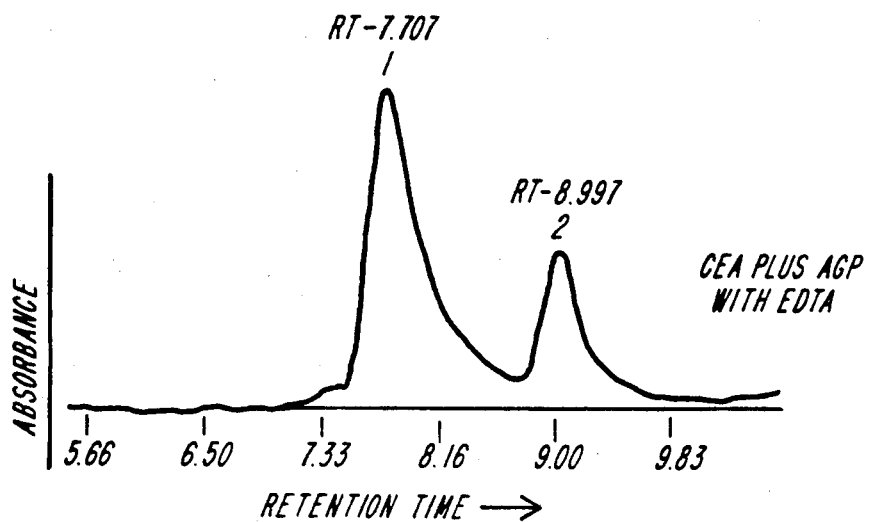
FIG. 4A–B is an optical scan of an HPLC of (A) alpha 1-acid glycoprotein (AGP)+CEA in the presence of EDTA, and (B) CEA+CBP in the presence of $CaCl_2$.
Figure 4B:
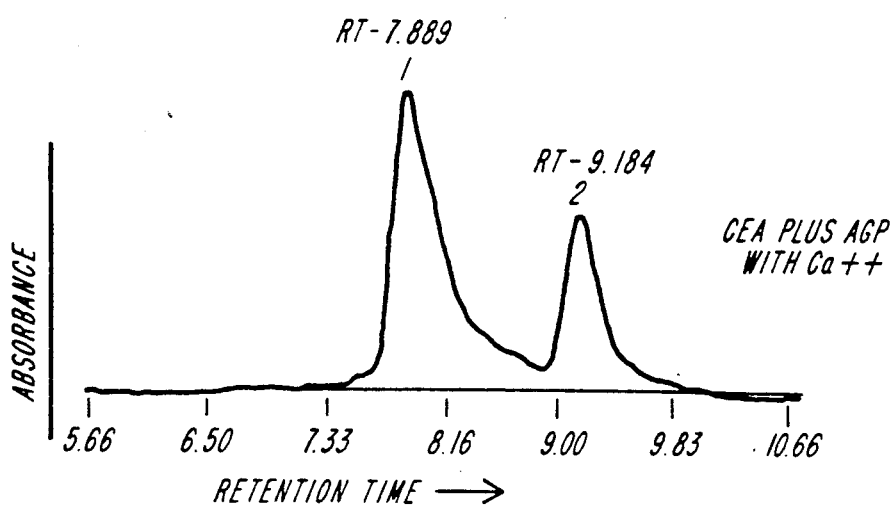

These isolated CBPs were further distinguished from AGP by HPLC. Like the CBPs, AGP does not bind CEA in the absence of calcium (presence of EDTA) (FIG. 4A). However, unlike the CBPs, AGP does not bind CEA in the presence of calcium ions (FIG. 4B). These CBPs have also been distinguished from CRP and SAP by isoelectric focusing.

A partial sequence of the 20 kD and 21 kD CBPs was obtained and is set forth in the Sequence Listing as SEQ ID NO:2 and SEQ ID NO:4, respectively. These partial sequences were found to have no homology with CEA or AGP. However, some sequence homology was found with the serum amyloid P protein (SAP) (FIG. 5), and with the C-reactive protein (CRP) (FIG. 6). These sequence analyses were performed using the Wisconsin Program Protein Data Base (Genetics Computer Group, University of Wisconsin Biotechnology Center, 1710 University Avenue, Madison, Wis. 53705).

SAP is a normal plasma component. It is an $\alpha$-1 glycoprotein composed of ten 23-25.5 kD subunits non-covalently linked as a double pentamer. The serum level of SAP in patients with various clinical types of amyloidosis, connective tissue diseases, and bacterial pneumonia does not differ significantly from normal values. Likewise, the serum level of patients with carcinoma of the colon do not differ from healthy individuals in the serum level of SAP (Levo et al. (1982) J. Immunol. Meth. 50:17-31). However, patients with carcinoma of the breast do have significantly increased serum concentrations of SAP which correlate with the severity of the disease (Levo et al. (Scand. J. Immunol. (1986) 24:147-151).

CRP, a dipentamer of 21 kD subunits, has a strong sequence homolgy with SAP. Both proteins undergo calcium-dependent ligand binding, are composed of non-covalently linked subunits, and share a similar pentagonal disc-like molecular form (Pepys (1982) Eur. J. Rheumatol. Inflamm. 5:386). In addition, they share at least about 60% homology of amino acid sequence. However, unlike SAP, CRP is an acute phase reactant in humans. Its concentration rises rapidly following acute tissue injury, infection, or inflammation, and it is often persistently elevated in cases of malignant neoplasia.

The sequence homology between the 20 kD and 21 kD CBPs, and CRP and SAP, respectively, raises the possibility that these proteins are related in structure and/or function as cancer markers.

Among the uses of the 20 kD and 21 kD CBPs are methods of detecting and treating carcinoma. The method of detection involves the administration to the subject of a pharmaceutical formulation including the 20 kD or 21 kD CBP, or CEA-binding fragments thereof, in a physiologically acceptable carrier. A biological sample is then taken. This sample may be ascites fluid, whole blood, serum, bile, saliva, sputum, lymphoid tissue, or tumor tissue. The concentration of CEA in this sample is measured. This measurement can be accomplished by any number of known tests for CEA including an immunoassay (e.g., Roche ELISA, Hoffman-La Roche, Nutley, N.J.) activity assay, immunoassay, quantitative electrophoresis, and the like. The concentration of CEA in the biological sample is then compared with a predetermined threshold level of CEA indicative of carcinoma. This threshold CEA concentration can be determined by administering a CBP to two statistically significant groups of people, one with carcinoma, and one that is disease-free. By way of example, the value of the threshold level may be the point at which the measured CEA concentration curves of these two groups intersect.

CBPs may also be used in the treatment of carcinoma as follows. A CBP is administered in a pharmaceutically acceptable carrier to a subject afflicted with carcinoma. The CBP binds CEA present in the subject, thereby inhibiting the metastatic proliferation of carcinoma cells which occurs as a result of CEA binding to CEA receptors on various organs (see, e.g., Toth et al. (1985) Cancer Res. 43:342-397; Toth et al. (1988) Biochem. Soc. Trans. 16:1027-1028; Toth et al. (1989) J. Leukocyte Biol. 45:370-376; and Hostetter et al. (1990) J. Natl. Cancer Insti. 82:380-385). The concentration of calcium in various body tissues is high enough to enable efficient binding.

The provision of a CBP in both methods of use can be accomplished by purification from a subject inflicted with carcinoma. Alternatively, given the sequence of these proteins isolated from body tissues, the CBPs may be prepared by recombinant DNA technology (see. e.g., Maniatis et al., *Molecular Cloning, A Laboratory Manual* (1982) Cold Spring Harbor Laboratory, Cold Spring Harbor, N.Y.), or by automated or manual biochemical peptide synthesis.

Effective dosages of the CBPs and modes of their administration in the detection and treatment of carcinoma can be determined by routine experimentation. The pharmaceutical formulation suitable for injectable use include sterile aqueous solutions or dispersions and sterile powders for the extemporaneous preparation of sterile injectable solutions or dispersions. In all cases the formulation must be sterile and must be fluid to the extent that easy syringability exists. It must be stable under the conditions of manufacture and storage and may be preserved against the contaminating action of microorganisms, such as bacteria and fungi. The carrier can be a solvent or dispersion medium containing, for example, water, polyol (for example, glycerol, propylene glycol, liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In some cases, it may be preferable to include isotonic agents, for example, sugars or sodium chloride. Prolonged absorption of the injectable CBPs can be brought about by the use in the compositions of agents delaying absorption.

Sterile injectable solutions are prepared by incorporating the CBPs in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from previously sterile-filtered solution thereof.

The CBP may be administered parenterally or intraperitoneally. Solutions of the CBP as pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The CBP also may be orally administered, for example, with an inert diluent or with an assimilable edible carrier, or enclosed in hard or soft shell gelatin capsules, or they may be compressed into tablets, or incorporated directly with the food of the diet. For oral administration, the CBP may be incorporated with excipients and used in the form of ingestible tablets, buccal tablets, troches, capsules, elixirs, suspension syrups, wafers, and the like. Such compositions and preparations should contain at least 0.1% of the CBP. The percentage of the compositions and preparations may, of course, be varied. The amount of CBP in such useful compositions is such that a suitable dosage will be obtained.

The tablets, troches, pills, capsules and the like may also contain the following: excipients, such as dicalcium phosphate; a disintegrating agent; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. A syrup or elixir may contain the active compounds sucrose as a sweetening agent, methyl and propylparabens as preservatives, a dye and flavoring, such as cherry or orange flavor. Of course, any material used in preparing any dosage unit form should be pharmaceutically pure and Substantially non-toxic in the amounts employed. In addition, the CBP may be incorporated into sustained-release preparations and formulations.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Antibodies to the 20 kD and 21 kD proteins are also provided by the invention. Such antibodies can be easily produced by one with ordinary skill in the art. For example, a purified CBP isolate from a subject afflicted with carcinoma as an antigen can be used as an antigen. Mice, goats, rabbits, or other animals can be challenged by injection with a solution of such an isolate emulsified in complete Freund's adjuvant at weekly intervals. After the initial injection, the booster injections can be administered without adjuvant or emulsified in incomplete Freund's adjuvant. Alternatively, synthetic or genetically engineered analogs or fragments of the CBP produced by recombinant DNA or biochemical techniques can be used as immunogens. An innoculum containing a relatively pure CBP sample isolated as described above along with Freund's adjuvent can be injected into a rabbit, mouse, rat, goat, or any mammal to produced monoclonal antibodies.

Monoclonal antibodies to a CBP or active binding fragments of such antibodies can be generated by applying generally known cell fusion techniques (cf. Kohler and Milstein (1976) *Eur. J. Immunol.* 6:511–519; and M. Shulman et al. (1978) *Nature* 276:269–270, herein incorporated by reference) to obtain a hybridoma producing the monoclonal antibody. Optionally, the monoclonal antibody may be subjected to proteolysis to obtain an active Fab, F(ab')$_2$, or Fv fragment.

More specifically, monoclonal antibodies are prepared by obtaining mammalian lymphocytes (preferably spleen cells), committing the lymphocytes to produce antibodies (e.g., by immunizing the mammal with the particular antigenic determinant of interest beforehand), fusing the lymphocytes with myeloma (or other immortal) cells to form hybrid cells, and then culturing a selected hybrid cell colony in vivo or in vitro to yield antibodies which are identical in structure and specificity.

In particular, monoclonal antibodies to a CBP can be raised by employing a purified CBP isolate from a subject afflicted with carcinoma as an antigen. Mice or other animals can be challenged by injection with a solution of such whole cells emulsified in complete Freund's adjuvant at weekly intervals. After the initial injection, the booster injections can be administered without adjuvant or emulsified in incomplete Freund's adjuvant. Alternatively, synthetic or genetically engineered analogs or fragments of the CBP produced by recombinant DNA or biochemical techniques can be used as immunogens.

Serum samples from the immunized animal can be analyzed by an enzyme linked immunoabsorbent assay ("ELISA") or the like for antibody reaction with the immunization agent. Animals that exhibit antibodies titers are sacrificed and their spleens homogenized. Alternatively, the spleen cells can be extracted and the antibody-secreting cells expanded in vitro by culturing with a nutrient medium. The spleen cells are then fused with myeloma (or other immortal) cells by the above-referenced procedure of Kohler and Milstein. The hybridomas so produced are screened (i.e., cloned by the limiting dilution procedure of the above-referenced Baker et al. article) to select a cell line producing antibodies which react with human α chain receptor proteins.

Large scale antibody production can be obtained from such anti-CBP-producing cell lines by various techniques, including the induction of ascites tumors (e.g., after priming with pristane) and the purification of such antibodies from the ascites fluid by Protein A-Sepharose affinity chromotography. For a further description of general hybridoma production methods, see Oi and Herzenberg, "Immunoglobulin-Producing Hybrid Cell Lines" in *Selected Methods in Cellular Immunology* (Mishell and Shiigi, Ed., W. H. Freeman & Co., 1980); and Scearce and Eisenbarth (1983) *Meth. Enzymol.* 103:459-469; and U.S. Pat. No. 4,411,933 issued to Gillis on Oct. 25, 1986, herein incorporated by reference.

Human antibodies (i.e., those obtained from human-human or human-animal hybridoma) can be used as well as animal antibodies. For descriptions of human hybridoma production techniques, see U.S. Pat. No. 4,451,570 issued to Royston et al. on May 29, 1984; U.S. Pat. No. 4,529,694 issued to Lazarus et al. on Jul. 16, 1985 and Zurawski et al., "Continuously Proliferating Human Cell Lines Synthesizing Antibody of Predetermining Specificity" in *Monoclonal Antibodies* (Plenum Press, New York 1980), also incorporated by reference.

Active antibody fragments can be derived from the monoclonal antibodies disclosed herein by a number of techniques. For example, purified monoclonal antibodies can be cleaved with an enzyme such as pepsin, and then subjected to HPLC gel filtration. The appropriate fraction containing Fab, F(ab)$_2$, or Fv can then be collected and concentrated by membrane filtration or the like. For further description of general techniques for the isolation of active fragments, see for example, Khaw, et al., Vol. 23 *J. Nucl. Med.*, pp. 1011-1019 (1982), incorporated by reference.

The antibodies and antibody fragments used herein can be labeled preferably with radioactive labels by a variety of techniques other than the above-described Baker et al. technique. For example, the biologically active molecules can also be labeled with a radionucleotide via conjugation with the cyclic anhydride of diethylenetriamine penta-acetic acid (DTPA) or bromoacetyl aminobenzyl ethylamine diamine tetra-acidic acid (BABE). See Hnatowich et al., Vol. 220 *Science*, pp. 613-615 (1983) and Meares et al. (1984) *Analytical Biochemistry.* Vol. 142, pp. 68-78, incorporated by reference for further description of labeling techniques.

The instant invention also relates to a method for screening subjects for carcinoma. It includes subjecting a biological sample to at least one test selected from a plurality of tests, each of which is specific for a carcinoma cell. Useful biological samples include ascites fluid, whole blood, serum, bile, lymphoid tissue, or tumor tissue obtained from a subject afflicted with carcinoma. The method used to obtain these samples is dependent on the nature of the sample and would be known by a medical practitioner. Each test correlates the presence of a specific marker with the presence of a carcinoma cell, and in some instances, with a degree of differentiation of that cell.

The screening method of the present invention includes tests for tumor markers CEA, CA 19.9, NCA, AGP, CORA (U.S. patent application Ser. No. 441,368, now U.S. Pat. No. 5,204,450), and the CC glycoprotein (U.S. Pat. No. 4,921,789), as well as any additional marker which indicate the presence of carcinoma, such as CRP or SAP. The tests may be performed in a sequential manner until the presence of at least one marker has been proven.

The tests performed may be assays, for example, to determine enzyme-linked activity, or may be immunoassays which utilize an antibody specific for a particular marker (see, e.g., U.S. Pat. No. 4,892,933). For example, an antibody raised to a cancer marker can be adhered to an adsorbent via chemical modification and/or covalent linkage using a bifunctional cross-linking reagent.

This invention provides a convenient kit for screening biological samples for colorectal carcinoma. This kit includes antisera or purified polyclonal or monoclonal antibodies specific for the 20 kD and 21 kD CBPs, and antibodies for at least one other tumor marker such as the CC glycoprotein, CORA, NCA, CA 19.9, CEA, AGP, SAP, or CRP. These antibodies can be prepared by methods well known to those skilled in the art (see description above). Of course this kit may contain antigen binding fragments of such antibodies such as Fv, Fab, or F(ab)$_2$ fragments obtained by known proteolytic cleavage or recombinant DNA techniques. Screening may be performed by any immunoassay procedures known in the art such as, for example, radioimmunoassay, Western blot analysis, or nitrocellulose "dot" analysis.

The following examples illustrate the best mode of making and practicing the present invention, but are not meant to limit the scope of the invention, since alternative methods may be used to obtain similar results.

EXAMPLE 1

Purification of CBPs

CBPs were isolated from ascites fluid from patients with colorectal adenocarcinoma using the following procedure. Exogenous CaCl$_2$ was added to human ascites fluid to give a final concentration of 5 mM. The ascites was then incubated with an anti-CEA monoclonal antibody (Hybritech, San Diego, CA) coupled to an affinity gel (Affi-Gel 10; Bio-Rad). After an overnight incubation with agitation at 4° C., the immunoadsorbent plus ascites fluid was put onto a (Affigel 10, Biorad, Richmond, Ca.) column, and any unbound material allowed to flow into a waste tube. The column was washed with wash buffer containing calcium (0.1

M Tris, pH 7.4, 0.15 M NaCl, and 5 mM CaCl$_2$) to remove any unadsorbed molecules. CBP was eluted from the column using elution buffer containing EDTA (0.1 M Tris, pH 7.4, 0.15 M NaCl, 10 mM EDTA).

EXAMPLE 2

Analytical Methods

A. HPLC

Figure 3D:
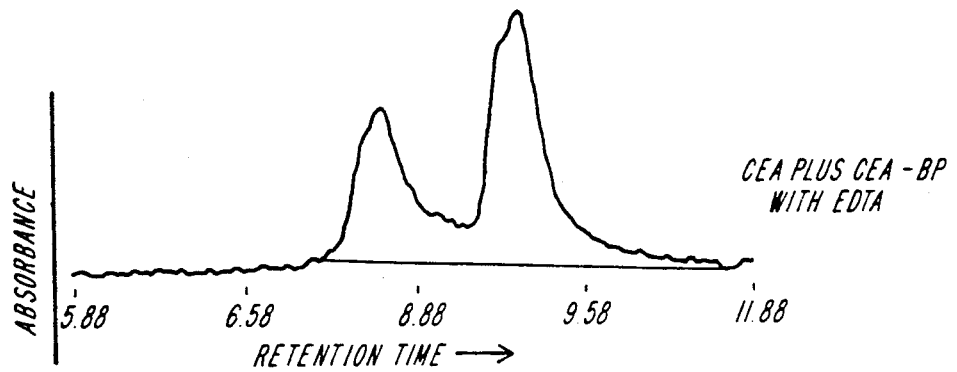

CBP extracted from human ascites fluid as described above was passed through a size exclusion column (GF-250, DuPont). The eluates were analyzed with the mobile phase (0.2 M sodium phosphate, pH 7.0, 0.005% sodium azide) at a flow rate of 1 ml/min and detection at 280 nm. The resulting elution profiles are shown in FIGS. 3A-3D. CBP migrates with CEA in the presence of calcium (FIG. 3C), while in the absence of calcium (presence of EDTA), it migrates as a separate peak (FIG. 3D).

B. Protein Sequencing

Samples were prepared for amino acid sequence analysis as follows. CBPs purified as described in EXAMPLE 1 were electrophoresed on an SDS-polyacrylamide gel (10-20% Mini-Gel, ISS, Newton, Ma.) according to the method of Laemmli (Nature (1970) 227:680-685) The proteins on the gel were then electrotransferred to an Immobilon TM P Transfer Membrane (Millipore) with transfer buffer (25 mM Tris, pH 8.3, 192 mM glycine, and 15% methanol v/v) according to the method of Towbin et al. (Proc. Natl. Acad. Sci (USA) 76:4350-4354). After staining the membrane with Coomassie Blue, it was washed several times with distilled water to remove traces of transfer buffer. The photograph of the stained membrane is shown in FIG. 2. Two proteins are present having molecular weights of 21 kD and 20 kD.

A duplicate gel was stained with periodic acid-Schiff base reagent (PAS) according to the method of Barber et al. (*Biochem.* (1971) 10:4711). This procedure demonstrated that the 21 kD protein is glycosylated.

The CBP bands were excised from the gel and mechanically sequenced according to the method of Matsudaria (*J. Biol. Chem.* (1988, 262:10035-10038) using an Applied Biosystems 477A protein sequencer. The resulting sequence obtained from the 20 kD CBP is forth in the Sequence Listing as SEQ ID NO: 4. The sequence obtained from the 21 kD CBP is shown in the Sequence Listing as SEQ ID NO:2.

EXAMPLE 3

Binding Assays

Affinity purified CBP was tested for the ability to bind to CEA in the presence of calcium ions as follows. Varied amounts of CBP was mixed with 5-10 µl CEA (100 µg/ml) CEA in the presence of 5 mM CaCl$_2$. The sample was then run on an HPLC sizing column (DuPont GF-250), and the elution profile was recorded (FIG. 3C).

The appearance of a single peak with a retention time of about 8.5 min and the absence of a peak at about 9.4 min suggests the formation of a complex between CEA and CBP. In control experiments (FIG. 3D) where CEA and CBP were mixed in the absence of Ca$^{2+}$ (EDTA added), two peaks with retention times similar to that of CEA (FIG. 3A) and that of CBP (FIG. 3B) were observed.

EXAMPLE 4

Isoelectric Focusing

The 20 kD CBP, the 21 kD CBP, CRP, and SAP were radioiodinated with $^{125}$I using the chloramine T procedure of Greenwood et al (Biochem. J. (1963) 89:114-123) to procure a specific activity of about 6-10 mCi/mg. Focusing was carried out in agarose gels essentially as described by Saravis et al (Immunol Meth (1979) 29:91-96). Radiolabelled protein was detected by audoradiography using Kodak X-OMAT film.

EXAMPLE 5

Assay for CEA

NUNC-Immuno Plates (Naperville, IL) were coated with 500 ng/well CEA mAb in carbonate buffer (0.05 of sodium carbonate, ph 9.6), and were incubated overnight (ON) at 4° C. The plates were washed with phosphate buffered saline (PBS) containing 1% (wt/vol) bovine serum albumin (BSA) and 0.5% (vol/vol) Tween 20 (PBS-BSA-TWEEN). They were then treated with 2% BSA in PBS for two hours at 4° C. to block any remaining sites on the plate. Antigen and high CEA serum standards were diluted and added to the appropriate wells at 50 µl/well. The plates were incubated ON at 4° C., and then washed with PBS-BSA-TWEEN buffer. 50 µl/well biotin-labelled anti-CEA monoclonal antibody (lot no. E50713-103; 2.5 µg/ml) was added and incubated for 3 hours at 37° C. The plates are washed with PBS-BSA-TWEEN. Stepavidin peroxidase-conjugated horse radish peroxidase (HRP) was added (diluted according to the concentration of the lot), and the plate incubated for 1 hour at 37° C. The plates were then washed with PBS-BSA-TWEEN. They were developed with orthophenylenediamine (Sigma, St. Louis, Mo.) and read with a spectrophotometer at 495 nm.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

We claim:

1. An isolated protein that specifically binds carcinoembryonic antigen (CEA), or a CEA-binding fragment of said protein,
   said CEA-binding protein (CBP) having a molecular weight of about 20 kD as determined by SDS-polyacrylamide gel electrophoresis, and binding CEA in the presence of a divalent cation in vitro.

2. The protein of claim 1 comprising the amino acid sequence set forth in the Sequence Listing as SEQ ID NO:4.

3. The protein or fragment of claim 1 further comprising a label attached thereto.

4. The protein or fragment of claim 3 wherein said label is selected from the group consisting of radioactive isotopes, enzymes, stable free radicals, coenzymes, fluorescent groups, chemiluminescent groups, toxins, and colorimetric groups.

5. An isolated protein that specifically binds carcinoembryonic antigen (CEA),
   said CEA-binding protein (CBP) having a molecular weight of about 20 kD as determined by SDS-polyacrylamide gel electrophoresis, and binding CEA in the presence of a divalent cation in vitro.

6. The protein of claim 5 comprising the amino acid sequence set forth in the Sequence Listing as SEQ ID NO:4.

7. The protein of claim 5 further comprising a label attached thereto.

8. The protein of claim 7 wherein said label is selected from the group consisting of radioactive isotopes, enzymes, stable free radicals, coenzymes, fluorescent groups, chemiluminescent groups, toxins, and colorimetric groups.

9. A device comprising:
(a) a support; and
(b) at least a CEA-binding fragment of said CBP of claim 1 bound to said support.

10. The device of claim 9 wherein said CBP comprises the amino acid sequence set forth in the Sequence Listing as SEQ ID NO:4.

11. A method of detecting carcinoma comprising the steps of:
(a) administering to a subject a pharmaceutical formulation comprising a carcinoembryonic antigen binding polypeptide (CBP) or fragment thereof in a physiologically acceptable carrier, said CBP having a molecular weight of approximately 20,000 daltons on SDS-polyacrylamide gels, and said CBP or said fragment thereof binding CEA in the presence of a divalent cation in vitro;
(b) obtaining a biological sample from said subject;
(c) measuring the concentration of CEA in said biological sample; and
(d) comparing said CEA concentration with a predetermined threshold concentration of CEA indicative of the presence of carcinoma.

12. The method of claim 11 wherein said administering step (a) comprises administering to the circulation of said subject a pharmaceutical formulation comprising a CEA-binding fragment of said CBP.

13. The method of claim 11 wherein said administering step comprises administering to the circulation of said subject a pharmaceutical formulation including a CBP comprising the amino acid sequence set forth in the Sequence Listing as SEQ ID NO:4.

14. The method of claim 11 wherein said administering step comprises administering said formulation to said subject by injection.

15. The method of claim 11 wherein said obtaining step comprises obtaining a sample selected from the group consisting of whole blood, serum, bile, saliva, sputum, lymphoid tissue, tumor tissue, and ascites fluid.

16. The method of claim 11 wherein said measuring step further comprises conducting an assay for CEA on said sample.

17. The method of claim 16 wherein said conducting step further comprises conducting an immunoassay for CEA.

18. An antibody or fragment thereof that specifically binds a carcinoembryonic antigen (CEA)-binding protein or CEA-binding fragment thereof, said CEA-binding protein having a molecular weight of about 20 kD as determined by SDS-polyacrylamide gel electrophoresis, and binding CEA in the presence of a divalent cation in vitro.

19. The antibody of claim 18 wherein said antibody is a monoclonal antibody.

20. A method of detecting carcinoma comprising the steps of:
(a) subjecting a biological sample from a subject to a test indicating the presence of a cancer marker, said marker comprising a carcinoembryonic antigen binding protein (CBP) that binds carcinoembryonic antigen (CEA) in the presence of a divalent cation in vitro, and has a molecular weight of about 20,000 daltons as determined by SDS-polyacrylamide gel electrophoresis, and
(b) screening said sample for the presence of said CBP, the presence of said CBP being indicative of the presence of carcinoma in said subject.

21. The method of claim 20 wherein said subjecting step further comprises subjecting a biological sample to a test indicating the presence of a cancer marker, said marker comprising the amino acid sequence set forth in the Sequence Listing as SEQ ID NO:4.

22. The method of claim 20 wherein said subjecting step further comprises a biological sample to an immunoassay utilizing an antibody that specifically binds said CBP.

23. The method of claim 20 wherein said subjecting step comprises subjecting a biological sample selected from the group consisting of whole blood, serum, bile, ascites fluid, saliva, sputum, lymphoid tissue, and tumor tissue to a test indicating the presence of a cancer marker.

24. A kit for screening a patient for carcinoma, said kit comprising an antibody specific for a carcinoembryonic antigen binding protein (CBP) or a CBP-binding fragment thereof, said CBP having a molecular weight of about 20,000 daltons on SDS-polyacrylamide gels, and binding carcinoembryonic antigen (CEA) in the presence of a divalent cation in vitro.

said kit further comprising an antibody or binding fragment thereof specific for a carcinoma marker selected from the group consisting of carcinoma orosomucoid-related antigen (CORA), carcinoembryonic antigen (CEA), CA 19.9, non-specific cross-reacting antigen (NCA), and alpha-1 acid glycoprotein (AGP).

25. The kit a claim 24 wherein said antibody specific for said CBP is a monoclonal antibody.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:

( A ) LENGTH: 225 amino acids
        ( B ) TYPE: amino acid
        ( D ) TOPOLOGY: linear ( i i ) MOLECULE TYPE: protein ( v i i ) FEATURE:
        ( A ) NAME/KEY: Serum amyloid P component ( x ) PUBLICATION INFORMATION:
        ( A ) AUTHORS: Mantzouranis, Evanelia C.
                Dowton, S. Bruce
                Whitehead, Alexander S.
                Edge, Michael D.
                Bruns, Gail A. P.
                Colten, Harvey R.
        ( B ) TITLE: Human Serum Amyloid P Component
        ( C ) JOURNAL: Journal of Biological
                Chemistry
        ( D ) VOLUME: 260
        ( E ) ISSUE: 12
        ( F ) PAGES: 7752-56
        ( G ) DATE: 25 JUN 1985

( x i ) SEQUENCE DESCRIPTION: SEQ ID NO:1:

Met Glu Lys Leu Leu Leu Cys Phe Leu Val Leu
                  5                   10
Thr Ser Leu Ser His Ala Phe Gly Gln Thr Asp
            15                  20
Met Ser Arg Lys Ala Phe Val Phe Pro Lys Glu
        25                  30
Ser Asp Thr Ser Tyr Val Ser Leu Lys Ala Pro
    35                  40
Leu Thr Lys Pro Leu Lys Ala Phe Thr Val Cys
45                  50                      55
Leu His Phe Tyr Thr Glu Leu Ser Ser Thr Arg
                60                      65
Gly Tyr Ser Ile Phe Ser Tyr Ala Thr Lys Arg
            70                  75
Gln Asp Asn Glu Ile Leu Ile Phe Trp Ser Lys
        80                      85
Asp Ile Gly Tyr Ser Phe Thr Val Gly Gly Ser
    90                  95
Glu Ile Leu Phe Glu Val Pro Glu Val Thr Val
100                 105                     110
Ala Pro Val His Ile Cys Thr Ser Trp Glu Ser
            115                     120
Ala Ser Gly Ile Val Glu Phe Trp Val Asp Gly
            125                 130
Lys Pro Arg Val Arg Lys Ser Leu Lys Lys Gly
        135                 140
Tyr Thr Val Gly Ala Glu Ala Ser Ile Ile Leu
    145                 150
Gly Gln Glu Gln Asp Ser Phe Gly Gly Asn Phe
155                 160                     165
Glu Gly Ser Gln Ser Leu Val Gly Asp Ile Gly
                170                     175
Asn Val Asn Met Trp Asp Phe Val Leu Ser Pro
            180                     185
Asp Glu Ile Asn Thr Ile Tyr Leu Gly Gly Pro
        190                     195
Phe Ser Pro Asn Val Leu Asn Trp Arg Ala Leu
    200                     205

```
Lys  Tyr  Glu  Val  Gln  Gly  Glu  Val  Phe  Thr  Lys
210                      215                      220

Pro  Gln  Leu  Trp  Pro
                    225
```

( 2 ) INFORMATION FOR SEQ ID NO:2:

( i ) SEQUENCE CHARACTERISTICS:
        ( A ) LENGTH: 40 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Xaa  Thr  Asp  Leu  Ser  Gly  Lys  Val  Phe  Val  Phe  Pro
                    5                        10

Xaa  Glu  Ser  Val  Thr  Asp  Xaa  Val  Asn  Leu  Ile  Thr
          15                      20

Pro  Leu  Glu  Lys  Pro  Leu  Gln  Xaa  Phe  Thr  Xaa  Ser
25                       30                       35

Xaa  Xaa  Ala  Tyr
               40
```

( 2 ) INFORMATION FOR SEQ ID NO:3:

( i ) SEQUENCE CHARACTERISTICS:
        ( A ) LENGTH: 223 amino acids
        ( B ) TYPE: amino acid
        ( D ) TOPOLOGY: linear ( i i ) MOLECULE TYPE: protein ( v i i ) FEATURE:
        ( A ) NAME/KEY: C-reactive protein ( x ) PUBLICATION INFORMATION:
        ( A ) AUTHORS: Lei, Ke-Jian
                  Liu, Teresa
                  Zon, Gerald
                  Soravia, Emilia
                  Liu, Teh- Yung
                  Goldman, Neil D.
        ( B ) TITLE: Genomic Sequence for Human
                C-reactive Protein
        ( C ) JOURNAL: Jouranl of Biological
                Chemistry
        ( D ) VOLUME: 260
        ( E ) ISSUE: 24
        ( F ) PAGES: 13377-83
        ( G ) DATE: 25 OCT 1985

( x i ) SEQUENCE DESCRIPTION: SEQ ID NO:3:

```
Met  Asn  Lys  Pro  Leu  Leu  Trp  Ile  Ser  Val  Leu
                    5                        10

Thr  Ser  Leu  Leu  Glu  Ala  Phe  Ala  His  Thr  Asp
               15                       20

Leu  Ser  Gly  Lys  Val  Phe  Val  Phe  Pro  Arg  Glu
          25                       30

Ser  Val  Thr  Asp  His  Val  Asn  Leu  Ile  Thr  Pro
     35                       40

Leu  Glu  Lys  Pro  Leu  Gln  Asn  Phe  Thr  Leu  Cys
45                       50                       55

Phe  Arg  Ala  Tyr  Ser  Asp  Leu  Ser  Arg  Ala  Tyr
                    60                       65

Ser  Leu  Phe  Ser  Tyr  Asn  Thr  Gln  Gly  Arg  Asp
               70                       75
```

```
Asn Glu Leu Leu Val Tyr Lys Glu Arg Val Gly
         80              85

Glu Tyr Ser Leu Tyr Ile Gly Arg His Lys Val
     90              95

Thr Ser Lys Val Ile Glu Lys Phe Pro Ala Pro
100              105                      110

Val His Ile Cys Val Ser Trp Glu Ser Ser Ser
             115                 120

Gly Ile Ala Glu Phe Trp Ile Asn Gly Thr Pro
            125                 130

Leu Val Lys Lys Gly Leu Arg Gln Gly Tyr Phe
        135              140

Val Glu Ala Gln Pro Lys Ile Val Leu Gln Gly
    145              150

Glu Gln Asp Ser Tyr Gly Gly Lys Phe Asp Arg
155             160                      165

Ser Gln Ser Phe Val Gly Glu Ile Gly Asp Leu
                170                 175

Tyr Met Trp Asp Ser Val Leu Pro Pro Glu Asn
            180                 185

Ile Leu Ser Ala Tyr Gln Gly Thr Pro Leu Pro
        190                 195

Ala Asn Ile Leu Asp Trp Gln Ala Leu Asn Tyr
    200                 205

Glu Ile Arg Gly Tyr Val Ile Ile Lys Pro Leu
210                 215                  220

Val Trp Val
```

( 2 ) INFORMATION FOR SEQ ID NO:4:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: protein ( v i i ) FEATURE:

( x i ) SEQUENCE DESCRIPTION: SEQ ID NO:4:

```
Phe Gly Gln Thr Leu Met Gly Gly Lys Ala Phe
              5                       10

Val Phe Pro Lys Ser
             15
```